(12) United States Patent
Nair et al.

(10) Patent No.: US 9,238,051 B2
(45) Date of Patent: Jan. 19, 2016

(54) PLANT-DERIVED FORMULATIONS FOR TREATMENT OF HIV

(75) Inventors: Madhavan P. N. Nair, Coral Gables, FL (US); Zainulabedin M. Saiyed, Pleasant Hill, CA (US); Nimisha H. Gandhi, Pleasant Hill, CA (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 78 days.

(21) Appl. No.: 13/696,762

(22) PCT Filed: May 10, 2011

(86) PCT No.: PCT/US2011/035922
§ 371 (c)(1),
(2), (4) Date: Jan. 18, 2013

(87) PCT Pub. No.: WO2011/143218
PCT Pub. Date: Nov. 17, 2011

(65) Prior Publication Data
US 2013/0136808 A1    May 30, 2013

Related U.S. Application Data

(60) Provisional application No. 61/333,116, filed on May 10, 2010.

(51) Int. Cl.
*A61K 36/74* (2006.01)
*A61K 36/00* (2006.01)

(52) U.S. Cl.
CPC ...................................... *A61K 36/74* (2013.01)

(58) Field of Classification Search
None
See application file for complete search history.

(56) References Cited

U.S. PATENT DOCUMENTS

2009/0011052 A1 *   1/2009   Li et al. ........................ 424/728

FOREIGN PATENT DOCUMENTS

WO   WO-2005/030232 A2    4/2005
WO   WO 2005030232 A2 *   4/2005

OTHER PUBLICATIONS

Chang et al. (2000) Tetrahedron Letters 41 pp. 7157-7162.*
Karodi et al. (2009) Inter. J. Applied Res. in Nat. Prods. vol. 2(2): pp. 12-18.*
Patel et al. (2010) Inter. J. Phytomedicine 2: pp. 44-46.*
Rao et al. (2006) J. Ethnopharmacology 103: 484-490.*
Schinazi et al. (1990) Antiviral Research 13: pp. 265-272.*
Shekhar et al. (2010) IJRAP 1 (1): 126-130.*
Treitinger et al. (2000) Eur. J. Clin. Invest. 30: pp. 454-459.*
Ma et al. (2002) Phytother. Res. 16, 186-189.*
Sabde et al. (2011) J. Nat. Med. 65: 662-669.*
Ranjith et al. (2008) African J. Biotech. vol. 7(2): pp. 081-085.*
Palep, Role of herbal immunomodulators and antioxidants in recurrent pregnancy loss. <http://www.bhj.org/journal/2006_4803_july/html/org_res_455_464.html> (2006).

* cited by examiner

*Primary Examiner* — Chris R Tate
*Assistant Examiner* — Russell Fiebig
(74) *Attorney, Agent, or Firm* — Marshall, Gerstein & Borun LLP

(57) ABSTRACT

Disclosed herein are methods for treating mammals with HIV/AIDS comprising administering a therapeutically effective amount of a composition comprising an extract of *Rubia cordifolia*. The extract is preferably an alcohol extract, an aqueous extract, or mixtures thereof. The alcohol preferably comprises ethanol, isopropyl alcohol, or mixtures thereof.

3 Claims, 2 Drawing Sheets

PLANT-DERIVED FORMULATIONS FOR TREATMENT OF HIV

BACKGROUND

HIV (formally known as HTLV-III and lymphadenopathy-associated virus) is a retrovirus that is the cause of the disease known as AIDS (Acquired Immunodeficiency Syndrome), a syndrome where the immune system begins to fail, leading to many life-threatening opportunistic infections. HIV has been implicated as the primary cause of AIDS and can be transmitted via exposure to bodily fluids. In addition to percutaneous injury, contact with mucous membranes or non-intact skin with blood, fluids containing blood, tissue or other potentially infectious bodily fluids pose an infectious risk. Infection of human CD-4+T-lymphocytes with an HIV virus leads to depletion of this cell population, resulting in an immunodeficient state, and eventually opportunistic infections, neurological dysfunctions, neoplastic growth, and ultimately death. There are currently 18 drugs licensed and used for the treatment of HIV, and these drugs are divided into one of four classes depending on how they attack HIV. Drugs in the class of nucleoside/nucleotide reverse transcriptase inhibitors are AZT (zidovudine, Retrovir), ddI (didanosine, Videx), 3TC (lamivudine, Epivir), d4T (stavudine, Zerit), abacavir (Ziagen), and FTC (emtricitabine, Emtriva). Drugs in the class of non-nucleoside reverse transcriptase inhibitors are efavirenz (Sustiva) and nevirapine (Viramune). Drugs in the class of protease inhibitors are lopinavir/ritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), and tipranavir (Aptivus). Only one drug is available in the class of fusion inhibitor, T20 (enfuvirtide, Fuzeon). The antiretroviral drugs are usually combined into three-drug cocktails called highly active antiretroviral therapy or HAART. However, the above-mentioned drugs still cannot effectively treat AIDS.

*Rubia cordifolia*, often known as Common Madder or Indian Madder, is a species of flowering plant in the coffee family, *Rubiaceae*. It has been cultivated for a red pigment derived from roots.

International Publication No. WO 2005/030232 describes composition prepared by extracting pulverized powder from various plants to treat HIV and AIDS. U.S. Patent Application Publication No. 2009/0011052 describes a composition including extract powders from medicinal herbs to treat AIDS.

SUMMARY

Disclosed herein is a method of treating a person with HIV/AIDS comprising administering to the person a therapeutically effective amount of a composition comprising an extract of *Rubia cordifolia*. In one embodiment the composition consists of an extract of *Rubia cordifolia*. The composition can further comprise a pharmaceutically-acceptable carrier or excipient.

The extract can be an aqueous extract, an alcohol extract, or a mixture of both. Preferably, the alcohol comprises ethanol, isopropyl alcohol, and mixtures thereof.

The extract can prepared using water, organic solvent, or a mixture thereof. Preferred organic solvents are low molecular weight alcohols, halogenated hydrocarbons, organic ethers, low molecular weight esters, low molecular weight ketones, and mixtures thereof.

BRIEF DESCRIPTION OF THE FIGURES

For a more complete understanding of the disclosure, reference should be made to the following detailed description and accompanying drawings wherein.

DETAILED DESCRIPTION

Figure 1:
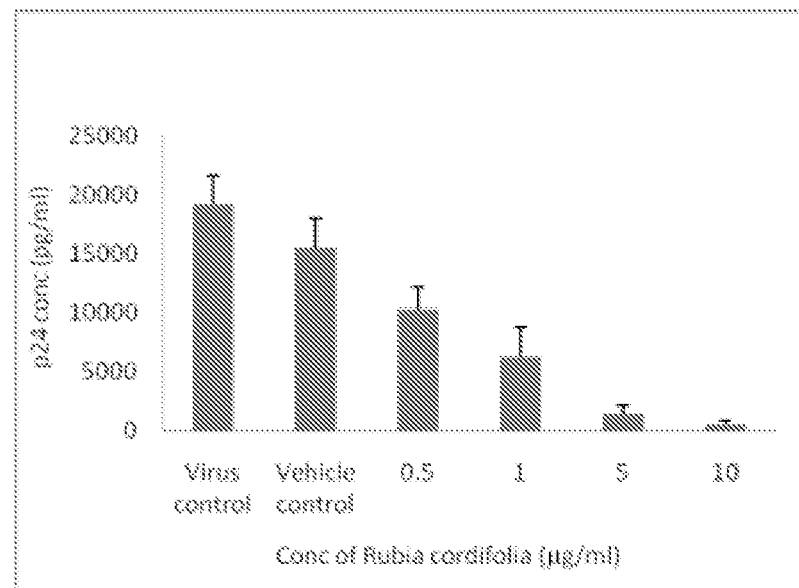
FIG. 1 is graph comparing the p24 antigen concentration at various concentrations of an ethanol extract of *Rubia cordifolia*.

Disclosed herein is a method for treating a person with HIV/AIDS comprising administering to the person a therapeutically effective amount of a composition comprising an extract of *Rubia cordifolia*.

An extract of *Rubia cordifolia* can be prepared in many ways, including alcohol extracts or other organic solvent extracts. A preferred extract is an alcohol extract of *Rubia cordifolia*. An alcohol extract of *Rubia cordifolia* can be prepared by extracting dry root powder of *Rubia cordifolia* with 75% v/v ethanol. For example, a 10 mg/ml sample can be prepared by suspending 10 mg dry root powder of *Rubia cordifolia* in one mL of 75% v/v ethanol, followed by rigorous vortexing. The suspension can be allowed to stand at room temperature for at least 2 hours and intermittently mixed with a vortex mixer. The supernatant can be collected as the alcohol extract of *Rubia cordifolia*. Alcohols used to prepare the extract can include low molecular weight alcohols, such as methanol or ethanol, or mixtures of low molecular weight alcohols with water. Organic solvents used to prepare the extract can include halogenated hydrocarbons, organic ethers, low molecular weight esters, low molecular weight ketones, other organic solvents, and combinations thereof.

The dry root powder of *Rubia cordifolia* can include collecting dried plants parts of *Rubia cordifolia* and refluxing the plant parts using water, organic solvent, or a mixture thereof. The refluxed plant parts can be filtered and the liquid collected. The liquid can be concentrated, and then dried to form a dry powder of *Rubia cordifolia*. Dried plant parts of *Rubia cordifolia* can include the leaves, root, or combinations thereof.

In some embodiments, the composition consists of an extract of *Rubia cordifolia*. The phrase "consists of" excludes other compounds that have anti-HIV activity. Thus, the composition consisting of an extract of *Rubia cordifolia* can include inert or non-active compounds, such as carriers or excipients.

The method can further include identifying a person in need of treatment for HIV/AIDS. Identifying a person in need of treatment can include testing for the presence of HIV.

The extract or components of the extract of *Rubia cordifolia* can be formulated into pharmaceutical formulations suitable for parenteral or oral administration. As used herein, "pharmaceutical formulation" is a composition of a pharmaceutically active drug, such as a biologically active compound or extract, that is suitable for parenteral or oral administration to a patient in need thereof and includes only pharmaceutically acceptable excipients, diluents, carriers and adjuvants that are safe for parenteral administration to humans at the concentrations used, under the same or similar standards as for excipients, diluents, carriers and adjuvants deemed safe by the Federal Drug Administration or other foreign national authorities. An oral pharmaceutical formulation may be in the form of a capsule, tablet, solution, suspension, and/or syrups, and may also comprise a plurality of granules, beads, powders, or pellets that may or may not be encapsulated. A parenteral pharmaceutical formulation may be in a ready-to-use solution form, concentrated form, or a lyophilized preparation that may be reconstituted with a directed amount of diluent suitable for parenteral injection such as water, salt solution, or buffer solution. Examples of parenteral routes include subcutaneous, intramuscular, intravascular (including intraarterial or intravenous), intraperitoneal, intraorbital, retrobulbar, peribulbar, intranasal, intrapulmonary, intrathecal, intraventricular, intraspinal, intracisternal, intracapsular, intrasternal or intralesional administration.

Tablets prepared for oral administration will in one aspect contain other materials such as binders, diluents, lubricants, disintegrants, fillers, stabilizers, surfactants, preservatives, coloring agents, flavoring agents and the like. Binders are used to impart cohesive qualities to a tablet, and thus ensure that the tablet remains intact after compression. Suitable binder materials include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, ethyl cellulose, hydroxyethyl cellulose, and the like), and Veegum. Diluents are typically necessary to increase bulk so that a practical size tablet is ultimately provided. Suitable diluents include dicalcium phosphate, calcium sulfate, lactose, cellulose, kaolin, mannitol, sodium chloride, dry starch and powdered sugar. Lubricants are used to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. Disintegrants are used to facilitate disintegration of the tablet, and are generally starches, clays, celluloses, algins, gums or crosslinked polymers. Fillers include, for example, materials such as silicon dioxide, titanium dioxide, alumina, talc, kaolin, powdered cellulose and microcrystalline cellulose, as well as soluble materials such as mannitol, urea, sucrose, lactose, dextrose, sodium chloride and sorbitol. Stabilizers are used to inhibit or retard drug decomposition reactions that include, by way of example, oxidative reactions. Surfactants may be anionic, cationic, amphoteric or nonionic surface active agents.

By a "therapeutically effective amount" of an extract of *Rubia cordifolia* is meant a sufficient amount of the extract or components of the extract to alleviate, modulate, or inhibit the negative or otherwise ill effects of HIV/AIDS infection. The extract of *Rubia cordifolia* can provide one or more of the following benefits: boost general immunity; increase CD4 counts in HIV-infected patients; reduce HIV viral loads in infected patients; and, reduce pathologies associated with HIV/AIDS progression.

In some embodiments, the composition excludes extracts or powders of one or more of the following plants: *Scutellaria Baicalensis Georgi, Cordyceps sinensis, ginsenoside, Terminalia Belerica, Alstonia Scholaris, Piper longum, Corallocarpus Epigaeus, Tinospora Cordifolia, Aloevera India, Hemidesmus Indica, Phyllanthus Emblica, Cinnamomum Zeylamicum, Citrullus Colocynthis Scrad, Zingiber officinale, Foeniculum valgare, Hyoscyamus niger, Succedania, Cyperus rotendus, Piper Longum, Commiphoria Mukul, Nordostachys, Withania Coagulans Dunal, Glycyrrhizaglabra, Pueraria Tuberosa, Santahim album, Artemisia Sieversiana, Eleeoacrpus ganitreus, Phyllanthus niruri, Berberidaceae Berberis Aristat D.C., Coriandrum Saticum, Vernonia anthelmintica, Carum Copticum, Azadirachta Indica A. Juss., Aristolochia Indica, Similax glabra, Andropogum citrates Rose, Mentha arvensis*, and *Aegle Marmelos*.

EXAMPLES

Example 1

Preparation of Alcohol Extraction 10 milligrams of dry root powder of *Rubia cordifolia* was suspended in 1 milliliter of 75% v/v ethanol. The suspension was rigorously vortexed. The suspension was allowed to stand at room temperature for at least 2 hours and intermittently mixed with a vortex mixer. The supernatant was collected to form the alcohol extract of *Rubia cordifolia*.

Example 2

Anti-HIV Activity Assay

The alcohol extract was tested in an in vitro HIV infection model. HIV infectivity was measured by estimating the amount of HIV-1 p24 antigen production. Anti-HIV activity of the *Rubia cordifolia* extract was tested by measuring p24 antigen production and HIV-LTR expression.

Peripheral blood mononuclear cells ("PBMC") from normal human subjects were isolated using Ficoll gradient method. The cells were then stimulated with phytoheam agglutinin for 48 hours. After 48 hours, the cells were harvested, washed, and resuspended in cell culture medium (RPMI 1640 medium available commercially from Sigma-Aldrich, St. Louis, Mo.) containing 10% fetal bovine serum and 2 µg/mL polybrene. The cells were incubated for 30 minutes, and then infected with native HIV-1 IIIB (available from NIH AIDS Research and Reference Reagent Program, Germantown, Md.) at a concentration of $10^3$ tissue culture infectious dose 50 ($TCID_{50}$) per mL for 2 hours.

The cells were then washed with phosphate buffered saline twice. $2\times10^6$ cells were plated in a 6-well plate. The alcohol extract of *Rubia cordifolia* was diluted to various concentrations and were added to the plated cells at 0.5 µg/mL, 1 µg/mL, 5 µg/mL, and 10 µg/mL of the alcohol extract of *Rubia cordifolia*. One well was left untreated and a control of just ethanol was added to another well to serve as controls. This preparation method was used to test both for p24 antigen production and HIV-1 LTR gene expression.

p24 Antigen Production

For testing for p24 antigen production, the cells were incubated for 7 days, and then harvested. The supernatant was collected for each well. The supernatant was tested for p24 antigen using a p24 ELISA kit (available commercially from ZeptoMatrix Corp., Buffalo, N.Y.). FIG. 1 details the p24 antigen concentration for each well, including the results from two controls (virus control and vehicle control). As the concentration of the alcohol extract of *Rubia cordifolia* increased, the concentration of p24 antigen decreased dramatically compared to the controls. Therefore, the extract of *Rubia cordifolia* significantly suppressed p24 antigen production indicating inhibition of HIV-1.

HIV-1 LTR Gene Expression

Figure 2:
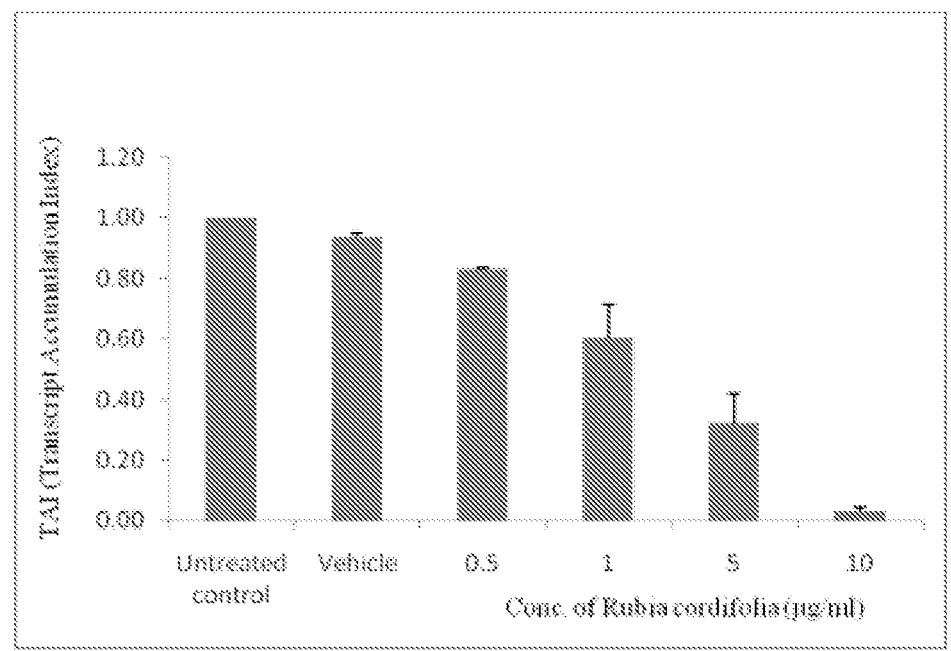
FIG. 2 is a graph comparing the transcript accumulation index for the HIV-1 LTR gene at various concentrations of an ethanol extract of *Rubia cordifolia*.

For testing for HIV-1 LTR gene expression, the cells were incubated for 24 hours, and then harvested. The RNA was extracted from the cell pellets. The RNA was reverse transcribed and followed by quantitative, real-time PCR against the LTR-RU5 and the housekeeping gene, β-actin, as internal controls. FIG. 2 details the transcript accumulation index ("TAI") for each well, including the results from two controls (untreated control and vehicle control). As the concentration of the alcohol extract of *Rubia cordifolia* increased, the TAI decreased dramatically compared to the controls. Therefore, the extract of *Rubia cordifolia* significantly suppressed HIV-TLR gene expression in a dose dependent manner in HIV-infected PBMCs.

Figure 3:
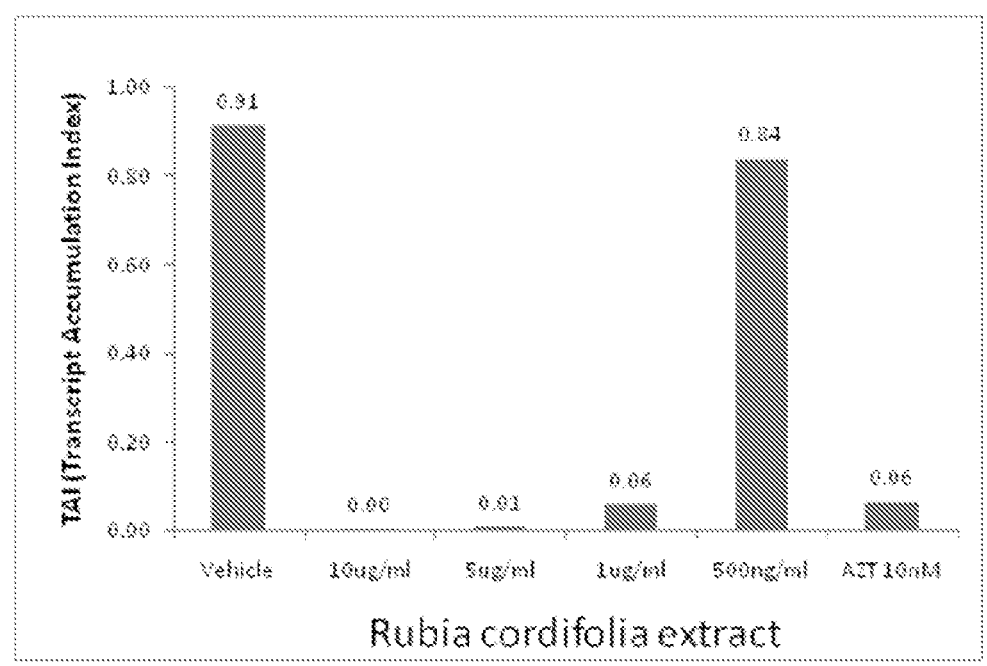
FIG. 3 is graph comparing the suppression of the HIV-1 LTR gene expression with 10 nM Azidothymidine and various concentration of the extract of *Rubia cordifolia*.

FIG. 3 is a comparison of 10 nM Azidothymidine with various concentrations of the extract of *Rubia cordifolia*. The extract at certain concentrations demonstrated either equal or improved suppression of the HIV-1 LTR gene expression.

Example 3a

Cytotoxicity and Inhibition of HIV-1 p24 Production of Samples 1-9

Various solvent extracts of the *Rubia cordifolia* plant, including extracts of the roots, leaves, and stems, were prepared and tested for anti-HIV activity using an in vitro HIV-1 infection model. Solvents included isopropyl alcohol, water, and a combination of both. Samples 1, 4, and 6 were aqueous extracts of the root of the *Rubia cordifolia* plant. Sample 2 was an aqueous extract of the whole *Rubia cordifolia* plant. Sample 3 was an aqueous extract of the stems of the *Rubia cordifolia* plant. Samples 5, 7, and 8 were hydro-alcoholic extracts of the root of the *Rubia cordifolia* plant. Sample 9 was an alcohol extract of the root of the *Rubia cordifolia* plant. PBMCs were infected with HIV-1 virus and subsequently cultured at two different concentrations of *Rubia cordifolia* extract, 10 µg/mL and 100 ng/mL. After 7 days of incubation, non-specific cytotoxicity of these samples was assessed by XTT cytotoxicity assay (Table 1) with respect to virus control and cell culture supernatants were harvested to determine HIV-1 p24 antigen concentration by ELISA (Table 2) with respect to virus control.

TABLE 1

Non-specific cytotoxicity of samples 1-9

| Sample | % Cytotoxicity | |
|---|---|---|
| | 10 µg/mL | 100 ng/mL |
| 1-6 | No activity | No activity |
| 7 | 47 | 0 |
| 8 | 52.2 | 0 |
| 9 | 7.2 | 2.4 |

TABLE 2

Inhibition of HIV-1 p24 production of samples 1-9

| Sample | % inhibition of HIV-1 p24 antigen production | |
|---|---|---|
| | 10 µg/mL | 100 ng/mL |
| 1 | 0 | 0 |
| 2 | 45 | 0 |
| 3 | 31 | 19 |
| 4 | 56 | 0 |
| 5 | 78 | 17 |
| 6 | 80 | 0 |
| 7 | 78 | 25 |
| 8 | 89 | 0 |
| 9 | 74 | 25 |

Example 3b

Cytotoxicity and Inhibition of HIV-1 p24 Production of Samples 10-18

Various solvent extracts of the *Rubia cordifolia* plant, including extracts of the roots, leaves, and stems, were prepared and tested for anti-HIV activity using an in vitro HIV-1 infection model. Solvents included isopropyl alcohol, water, and a combination of both. Sample 10 was an aqueous extract of the whole *Rubia cordifolia* plant. Samples 11 and 12 were aqueous extracts of the stems of the *Rubia cordifolia* plant. Sample 13-15 were aqueous extracts of the root of the *Rubia cordifolia* plant. Sample 16-18 were alcoholic extracts of the root of the *Rubia cordifolia* plant. PBMCs were infected with HIV-1 virus and subsequently cultured at two different concentrations of *Rubia cordifolia* extract, 10 µg/mL and 100 ng/mL. After 7 days of incubation, non-specific cytotoxicity of these samples was assessed by XTT cytotoxicity assay (Table 3) with respect to virus control and cell culture supernatants were harvested to determine HIV-1 p24 antigen concentration by ELISA (Table 4) with respect to virus control.

TABLE 3

Non-specific cytotoxicity of samples 10-18

| Sample | % Cytotoxicity | |
|---|---|---|
| | 10 µg/mL | 100 ng/mL |
| 10 | 0 | 0 |
| 11 | 26 | 10 |
| 12 | 36 | 19 |
| 13 | 45 | 25 |
| 14-15 | No activity | No activity |
| 16 | 17 | 0 |
| 17 | 97 | 15 |
| 18 | 99 | 31 |

TABLE 4

Inhibition of HIV-1 p24 production of samples 10-18

| Sample | % inhibition of HIV-1 p24 antigen production | |
|---|---|---|
| | 10 µg/mL | 100 ng/mL |
| 10 | 2.5 | 4.3 |
| 11 | 2.1 | 1.5 |
| 12 | 0.3 | 0 |
| 13 | 8.8 | 9.9 |
| 14 | 8.5 | 2.7 |
| 15 | 0 | 2.2 |
| 16 | 3.6 | 3 |

TABLE 4-continued

Inhibition of HIV-1 p24 production of samples 10-18

| Sample | % inhibition of HIV-1 p24 antigen production | |
|---|---|---|
| | 10 µg/mL | 100 ng/mL |
| 17 | 76.6 | 2.3 |
| 18 | 84.1 | 22.9 |

The extract of *Rubia cordifolia* has demonstrated anti-HIV activity. For example, the extract of *Rubia cordifolia* can suppress HIV-1 LTR gene expression. It can suppress p24 antigen production. The extract of *Rubia cordifolia* preferably provides greater than 45% inhibition of HIV-1 p24 antigen production, more preferably, greater than 55% inhibition of HIV-1 p24 antigen production, and most preferably, greater than 75% inhibition of HIV-1 p24 antigen production. The extract of *Rubia cordifolia* preferably provides greater than 45% non-specific cytotoxicity on peripheral blood mononuclear cells infected with HIV-1 virus, more preferably, greater than 50% non-specific cytotoxicity, and most preferably, greater than 75% non-specific cytotoxicity.

The foregoing description is given for clearness of understanding only, and no unnecessary limitations should be understood therefrom, as modifications within the scope of the invention may be apparent to those having ordinary skill in the art.

What is claimed is:

1. A method for treating HIV/AIDS in a subject in need thereof, the method comprising administering a composition consisting of a hydro-ethanolic extract of *Rubia cordifolia* to the subject in an amount effective to inhibit HIV-1 p24 antigen in the subject.

2. The method of claim 1, wherein the hydro-ethanolic extract is obtained from the roots of a *Rubia cordifolia* plant.

3. The method of claim 1, wherein the hydro-ethanolic extract is prepared by extracting dry root powder of *Rubia cordifolia* with 75% v/v ethanol.

* * * * *